United States Patent
Dunlap et al.

(10) Patent No.: US 11,424,014 B1
(45) Date of Patent: *Aug. 23, 2022

(54) ELECTRONIC MEDICAL RECORD TRANSFER SYSTEMS AND METHODS

(71) Applicant: United Services Automobile Association (USAA), San Antonio, TX (US)

(72) Inventors: Steven K. Dunlap, Boerne, TX (US); Michael Belko, Boerne, TX (US); Sharon Kay Haverlah, Bulverde, TX (US); Wesley Allen Arnold, Boerne, TX (US)

(73) Assignee: United Services Automobile Association (USAA), San Antonio, TX (US)

( * ) Notice: Subject to any disclaimer, the term of this patent is extended or adjusted under 35 U.S.C. 154(b) by 194 days.

This patent is subject to a terminal disclaimer.

(21) Appl. No.: 16/841,194

(22) Filed: Apr. 6, 2020

Related U.S. Application Data

(63) Continuation of application No. 14/989,702, filed on Jan. 6, 2016, now Pat. No. 10,622,101.

(51) Int. Cl.
*G16H 10/60* (2018.01)

(52) U.S. Cl.
CPC .................. *G16H 10/60* (2018.01)

(58) Field of Classification Search
CPC .............................. G06Q 50/24; G16H 10/60
See application file for complete search history.

(56) References Cited

U.S. PATENT DOCUMENTS

| | | |
|---|---|---|
| 6,014,081 A | 1/2000 | Kojima et al. |
| 2004/0225200 A1 | 11/2004 | Edmundson et al. |
| 2005/0125258 A1 | 6/2005 | Yellin et al. |
| 2006/0149140 A1 | 7/2006 | Eldridge |
| 2007/0004969 A1 | 1/2007 | Kong et al. |
| 2007/0156453 A1 | 7/2007 | Frielinghaus et al. |
| 2008/0021730 A1 | 1/2008 | Holla et al. |
| 2009/0132460 A1 | 5/2009 | Alemi |
| 2009/0209830 A1 | 8/2009 | Nagle et al. |
| 2011/0245633 A1 | 10/2011 | Goldberg et al. |
| 2012/0221345 A1 | 8/2012 | McClure et al. |

(Continued)

OTHER PUBLICATIONS

White, J.B.; "A Car That Takes our Pulse"; Wall Street Journal; Nov. 28, 2012.

(Continued)

*Primary Examiner* — John A Pauls
(74) *Attorney, Agent, or Firm* — Fletcher Yoder P.C.

(57) ABSTRACT

In one embodiment, one or more non-transitory, computer-readable mediums store computer instructions that, when executed by a processor, cause the processor to receive inputs from one or more request sources. The inputs include user credentials to an electronic medical record (EMR) source provider system. The computer instructions, when executed by the processor, also cause the processor to validate the credentials via communication with the EMR source provider system without an external authorization process, retrieve one or more EMRs from the EMR source provider system after the credentials are validated by the EMR source provider system, and store the one or more EMRs in a single data repository.

20 Claims, 3 Drawing Sheets

(56) References Cited

U.S. PATENT DOCUMENTS

| | | |
|---|---|---|
| 2014/0052464 A1 | 2/2014 | Ray |
| 2015/0326557 A1 | 11/2015 | Teramura et al. |
| 2015/0370994 A1 | 12/2015 | Madan et al. |
| 2016/0259977 A1* | 9/2016 | Asbun .................. A61B 5/1112 |
| 2016/0371786 A1 | 12/2016 | Kusens et al. |

OTHER PUBLICATIONS

Boyle, R.; "Ford Wants Your Next Car to Monitor Your Vital Signs as You Drive"; Popular Science; May 19, 2011.
HIMSS Board of Directors; "Definition of Interoperability"; HIMSS; Apr. 5, 2013.
"Step 5: Achieve Meaningful Use Stage 2 Patient Ability To Electronically View, Download & Transmit (VDT) Health Information"; http://www.healthit.gov/providers-professionals/achieve-meaningful-use/core-measures-2/patient-ability-electronically-view-download-transmit-vdt-health-information; Feb. 24, 2014; last accessed Jan. 6, 2016.
Dullabh, P. MD; Adler-Milstein, J. PhD; Hovey, L. MS; Jha, A. MD MPH; "Final Report Key Challenges to Enabling Health Information Exchange and How States Can Help"; NORC; Aug. 2014.
"The Top 5 roadblocks HIEs face"; http://www.govhealthit.com/news/top-5-roadblocks-hies-face; Nov. 14, 2011; last accessed Jan. 6, 2016.

* cited by examiner

ELECTRONIC MEDICAL RECORD TRANSFER SYSTEMS AND METHODS

CROSS-REFERENCE TO RELATED APPLICATION

This application is a continuation of U.S. patent application Ser. No. 14/989,702, entitled "ELECTRONIC MEDICAL RECORD TRANSFER SYSTEMS AND METHODS," filed Jan. 6, 2016, which is hereby incorporated by reference in its entirety for all purposes.

BACKGROUND

The present disclosure relates generally to electronic medical records, and more specifically, to systems and methods for acquiring, analyzing, and/or transferring electronic medical records.

Transfer of medical records has traditionally been complicated by a lack of interoperability among medical record systems, patient authorization, subsequent authentication, and so forth. Such transfers are complicated by time delays associated with coordinating systems, obtaining patient approval, and obtaining access via authentication. For example, authentication typically includes a person of authority governing access to medical records and permitting access for each request, which requires time and introduces delay. It is now recognized that this time delay exists irrespective of the sophistication of the electronic medical record. It is also recognized that further complications may be added by a lack of standardization in medical record content, which can create communication failures and delays.

BRIEF DESCRIPTION

In one embodiment, one or more non-transitory, computer-readable mediums store computer instructions that, when executed by a processor, cause the processor to receive inputs from one or more request sources. The inputs include user credentials to an electronic medical record (EMR) source provider system. The computer instructions, when executed by the processor, also cause the processor to validate the credentials via communication with the EMR source provider system without an external authorization process, retrieve one or more EMRs from the EMR source provider system after the credentials are validated by the EMR source provider system, and store the one or more EMRs in a single data repository.

In one embodiment, a method includes receiving inputs, via a processor, from one or more request sources. The inputs include user credentials to an electronic medical record (EMR) source provider system and a selection of a receiving provider system, and the one or more request sources include a patient portal or an electronic record source. The method also includes retrieving one or more EMRs from the EMR source provider system when the credentials are validated by the EMR source provider system without a separate authorization process, and transmitting the one or more EMRs to the receiving provider system.

In one embodiment, a system includes a server including a processor configured to receive inputs from one or more request sources. The inputs include user credentials to an electronic medical record (EMR) source provider system and one or more receiving provider systems, and the one or more request sources include a patient portal or an electronic record source. The processor is also configured to retrieve one or more EMRs from the EMR source provider system when the credentials are validated by the EMR source provider system, store the one or more EMRs in a single data repository, and transmit the one or more EMRs to the one or more receiving provider systems.

DRAWINGS

These and other features, aspects, and advantages of the present disclosure will become better understood when the following detailed description is read with reference to the accompanying drawings in which like characters represent like parts throughout the drawings, wherein.

Figure 4:
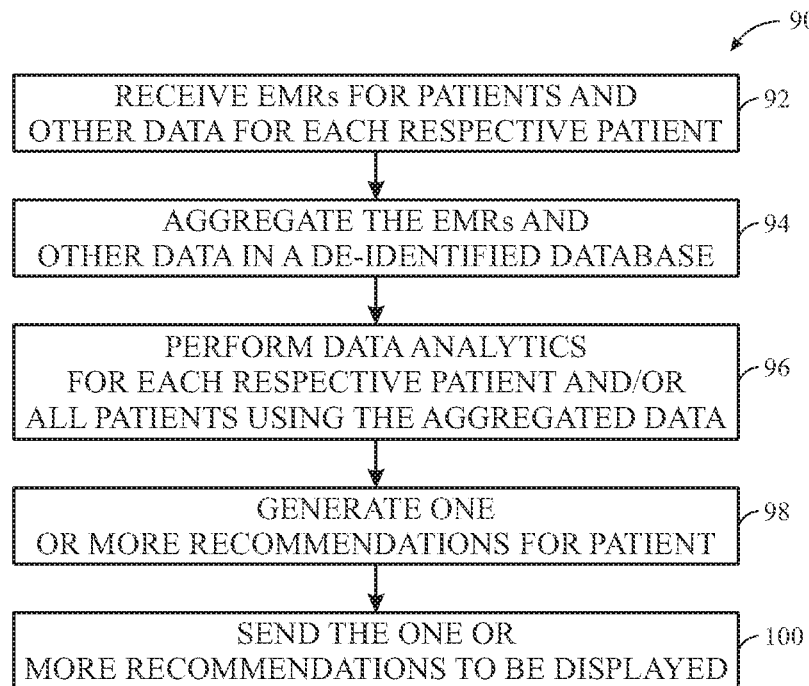
Figure 5:
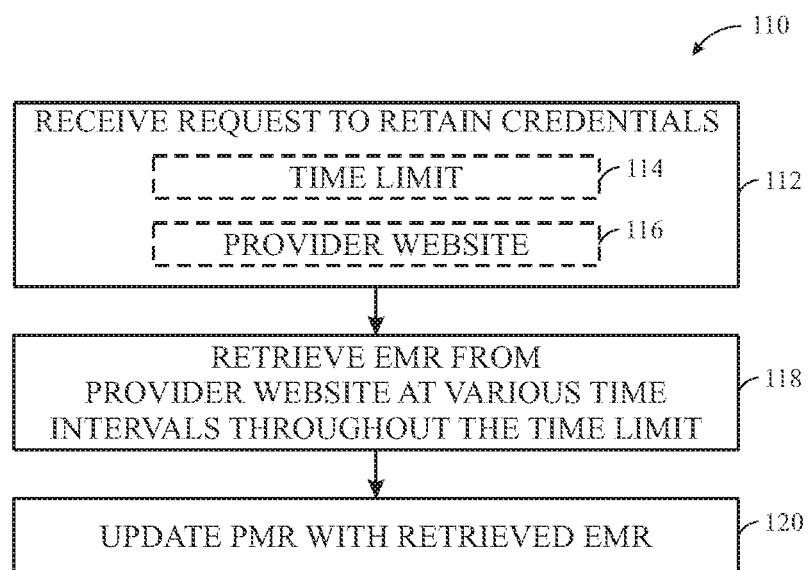

FIG. 4 is a process flow diagram illustrating an embodiment of a process of performing data analytics using aggregated EMRs and/or other data, in accordance with an aspect of the present disclosure; and FIG. 5 is a process flow diagram illustrating an embodiment of a process of automatically updating a personalized medical record for a patient using stored credentials, in accordance with an aspect of the present disclosure.

DETAILED DESCRIPTION

One or more specific embodiments of the present disclosure will be described below. In an effort to provide a concise description of these embodiments, all features of an actual implementation may not be described in the specification. It should be appreciated that in the development of any such actual implementation, as in any engineering or design project, numerous implementation-specific decisions must be made to achieve the developers' specific goals, such as compliance with system-related and business-related constraints, which may vary from one implementation to another. Moreover, it should be appreciated that such a development effort might be complex and time consuming, but would nevertheless be a routine undertaking of design, fabrication, and manufacture for those of ordinary skill having the benefit of this disclosure.

Present embodiments are generally related to an electronic medical record (EMR) system for acquiring, analyzing, and transferring EMRs. In some embodiments, the EMR system includes a software utility that may be a stand-alone application or service hosted in a server that is separately called by a request source (e.g., patient portal or electronic record source) or the EMR software utility may be wholly or partially integrated as a part of the request source. The EMR software utility may permit a user to view record content, download record content, and/or determine receivers of record content via the request source (e.g., patient portal). In some embodiments, the EMR software utility may be used during various processes (e.g., analysis of an arrangement to guarantee compensation for specified illnesses or death based on payment of a premium or compensation based on such an arrangement) involving acquisition of EMRs. Indeed, the EMR software utility may enable aggregating all EMR content for each user of the utility in a single repository. In some embodiments, the user may use the EMR software utility to retrieve and send electronic record content to other institutions (e.g., provider systems) irrespective of the format or manufacture of the receiving system. Thus, a lack of interoperability between systems may be addressed for a segment of a relevant industry (e.g., healthcare systems) that may benefit from accurate, timely, and secure records. Further, since the patient (e.g., user) is performing the request directly, no time consuming consent/authorization process is used. In some embodiments, the obtained electronic record content may be transformed by the EMR software utility into a common format for EMR data which is specific and valuable to certain entities (e.g., hospitals and healthcare payment guarantors), to reduce the time and work of extracting key information. In addition, such a format may be amenable to business rules which permit rapid and automated decision capability.

In some embodiments, a de-identified database (e.g., a database that excludes association of personal information with certain metrics or data) may be created from the content of the EMR imported by the EMR software utility. That is, EMR content that streams through the EMR software utility may be parsed, de-identified, and stored in the database such that group health records are accessible without allowing association of the data with specific individuals. The de-identified database may enable data mining of abstracted health data that may be useful for insurers, researchers, pharmaceutical manufacturers, and others. In some embodiments, the EMR software utility may perform correlations of record content for people that share similar characteristics (e.g., demographics, age, gender, nationality, common symptoms, genealogical disorders, history of illness, etc.) to a patient (e.g., the patient using the de-identified database) and generate one or more recommendations for the patient via the patient portal. As may be appreciated, accumulating all of the records of the patient enables storing the records in a single data repository for release to provider systems at the direction of the patient (e.g., without conventional consent and authorization process). Further, at the request of the patient, the EMR patient portal may retain credentials to various vendor websites (e.g., provider systems) for a specified time and may regularly update the records of the patient (e.g., by polling the websites for updated record content). Also, outbound requests and/or consents may be timed and managed at the discretion of the patient.

Figure 1:
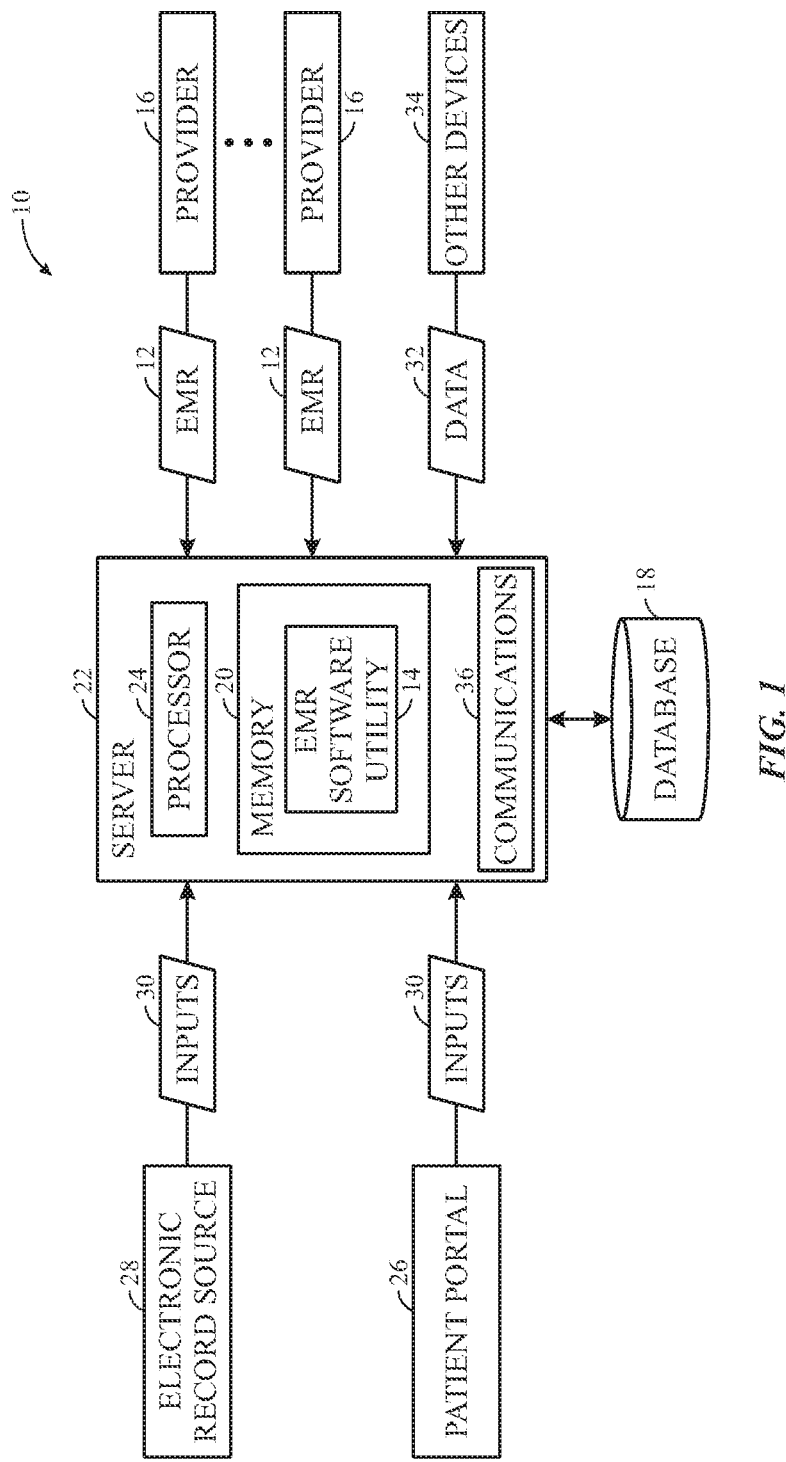
FIG. 1 is a block diagram of an embodiment of a system that may be utilized to acquire, process, and transfer electronic medical records (EMRs) using an EMR software utility, in accordance with an aspect of the present disclosure.

To help illustrate the manner in which the present embodiments may be used in a system, FIG. 1 is a block diagram of an embodiment of a system 10 that may be utilized to acquire, process, and transfer electronic medical records (EMRs) 12 using an EMR software utility 14. The EMR software utility 14 may enable transferring EMRs 12 from one provider system 16 to another provider system 16 or retrieving the EMRs 12 from one or more provider systems 16 and storing the EMRs 12 in a centralized data repository (e.g., database 18) to create a personalized medical record. Each provider system 16 may maintain a single secure connection with the server 22 when transferring the EMRs 12. A "personalized medical record" may refer to an aggregation of EMRs 12 for a single patient from disparate sources in a single data repository, such as database 18. The provider systems 16 may include service providers (e.g., healthcare providers, healthcare reimbursement guarantors), and the like. The database 18 may be stored locally in the memory 20 of the server 22 or remotely on another server.

Further, the EMR software utility 14 may de-identify the EMRs 12 when importing the EMRs 12 into the database 18 by removing any personal identifiers (e.g., name, social security number, birth date). In some embodiments, the de-identified information may be used by the EMR software utility 14 and/or other services to perform certain data analytics to provide recommendations to a patient or healthcare professional, determine trends among similarly situated individuals, or the like.

In some embodiments, the EMR software utility 14 may be stored on a memory 20 of a server 22 that also includes a processor 24 generally capable of storing and executing instructions to provide certain functionality described below. As noted above, the EMR software utility 14 may be a stand-alone service or application programming interface (API) that is called upon by a request source, such as a patient portal 26 and/or any suitable electronic record source 28, or the EMR software utility 14 may be wholly or partially encapsulated in the patient portal 26 or the electronic record source 28. The patient portal 26 may refer to a secure online website that provides access to patients to personal health information from anywhere with an Internet connection. An electronic record source may refer to a replication service that stores a copy of EMR content. In certain situations, the electronic record source may be called upon to provide the copy of the EMR content (e.g., when data at a service provider is corrupted). Further, the replication service may make requests to import EMR content when used by a provider system and the requests may be handled by the EMR software utility 14.

In accordance with the present disclosure, the server 22 may be a specialized computing device. In other embodiments, the server 22 may be a general purpose computing device, such as a laptop computer, a personal computer, a tablet, a mobile device, or a smart phone. The system 10 may be programmed to execute, via the processor 24, instructions (e.g., software modules, applications, apps) stored on the memory 20 to provide the functionality set forth below (e.g., retrieve, transmit, store, analyze, update, reformat, process EMRs 12 and/or perform data analytics). For example, in certain embodiments, the server 22 hosting the EMR software utility 14 may receive inputs 30 from the patient portal 26 and/or the electronic record source 28. The inputs 30 may include credentials of the user, such as username and password, for the provider system 16 associated with the patient portal 26 and/or the electronic record source 28. In some embodiments, the credentials of the user may be associated with the EMR source provider system (e.g., website) from which the EMRs 12 are requested. Additionally, the inputs 30 may include a designation of a receiving provider system 16 to receive the selected EMRs 12 to be transferred. In some embodiments, a selection of specific EMRs 12 to transfer may be input, a subset of content from certain EMRs 12 to transfer may be input, or the like. For example, a user may request to send information related to lab results from a system of a doctor that performed the lab work to a system for a company providing a health-based analysis or quote. In another example, for a member of a patient portal that is proceeding on a claim related to a guarantee of compensation for illness or the like, the EMR software utility 14 may enable the user to send information directly and rapidly between the appropriate provider systems 16.

In certain embodiments, the server 22 may receive the inputs 30 either directly or indirectly. For example, the server 22 may be configured to receive the inputs 30 from the user via information that the user previously provided to the patient portal 26 or via information recently entered by the user. In some embodiments, the inputs 30 may include information related to the health of the user. For example, the user may use the patient portal 26 to view the personalized medical record stored in the database 18 and to update certain information included in the personalized medical record. Additionally, the patient portal 26 may enable the user to directly input additional and/or otherwise unknown health related information to update the personalized medical record. That is, the user may input information such as age, blood pressure, heart rate, weight, height, allergies, medications, exercise, and/or any other health related data.

In certain embodiments, the user may use the EMR software utility 14 to transfer EMRs 12 between provider systems 16 and/or computing devices via the patient portal 26. For example, the user may enter the credentials to the EMR source provider system 16 where the EMRs 12 may be obtained and select a destination receiving provider system 16 from a list of cleared provider systems 16. In some embodiments, the providers may be accepted and cleared by a clearinghouse prior to being placed in the list of cleared provider systems 16. Further, in some embodiments, the EMR source provider system 16 may include a website, such as a patient portal for the EMR source provider. In some embodiments, the EMR software utility 14 may retrieve the desired EMR 12 from the source provider website using screen scraping techniques or the like. Further, the EMR software utility 14 may reformat the obtained EMR 12 into a common data format that complies with an expected format of the receiving provider system 16. The EMR software utility 14 may send the EMR file to the receiving provider system 16. As may be appreciated, typical time consuming authorization and authentication processes associated with traditional technology may be avoided using the disclosed techniques because the patient makes the request to transfer EMRs 12 directly through the patient portal 26. Further, the EMR software utility 14 alleviates the problem when provider systems 16 use different platforms because the EMR 12 may be reformatted into a common format that conforms to specified formats of electronic documents for each receiving provider system 16. Thus, Internet-centric and computer-centric issues with communication and delay are addressed by proceeding in accordance with present embodiments.

In certain embodiments, other data 32 may be received by the server 22 from other devices 34 over a network. In certain embodiments, the network may be wireless such that the server 22 receives the other data 32 via a wireless transmission. In other embodiments, the network may be a wired connection between the server 22 and the other devices 34. The other devices 34 may include one or more smartphones, wearables (e.g., bracelet, necklace, chip, tag, smartwatch), automobiles, another computing device, and the like. The data 32 may include data related to the health of the user. For example, a wearable that tracks steps taken by a user in a day and monitors heart rate, blood pressure, and/or temperature may send such data 32 to the EMR software utility 14 hosted by the server 22, which may update the personalized medical record of the user by storing the data 32 in the database 18. In another example, a user may use a smartphone to manually enter the data 32, such as measured blood pressure, heart rate, and the like, which can then be stored by the EMR software utility 14 in the appropriate EMRs 12 of the personalized medical record. In another example, a communicatively connected automobile may provide data 32 related to the amount of time the user spends driving in a car. Additionally, another computing device may supply an air quality to the EMR software utility 14, which may determine whether the user has any known allergies to warn the user. As should be appreciated, the EMR software utility 14 may use the provided data 32 in conjunction with the acquired EMRs 12 to perform certain data analytics and determine one or more recommendations for the user. Even further, the EMR software utility 14 may compare the data 32 and information included on the EMRs 12 with other similarly situated people (e.g., age, race, gender, occupation, health indicators, medical history) to provide one or more recommendations to the user via the patient portal 26, for example. Certain data may be weighted based on its nature (e.g., reliability) and the weighting may be utilized for analysis purposes. Further, the EMR software utility 14 may analyze the data 32 and other inputs to confirm authenticity and/or designate the nature of certain inputs. For example, actual physiological measurements from a wearable may be assigned a heavier authenticity weighting than a user's manual inputs from a laptop because the former are less susceptible to manipulation or error on the part of the user. Likewise, data provided by a healthcare provider may be weighted heavily when authenticity is confirmed.

The server 22 illustrated in FIG. 1 includes communication circuitry 36 that may enable the system 10 to communicate via wired (e.g., Ethernet) or wireless (e.g., cellular, WiFi, Bluetooth) network connections with the electronic record source 28, the patient portal 26, the provider systems 16, the database 18, and/or other devices 34 on the network. In certain embodiments, the server 22 may receive the inputs 17 via a connection (e.g., via WiFi or Bluetooth) to a smartphone or computer of the user. In other embodiments, the user may indirectly interact with the server 22 via a wearable, for example, when the user is not in physical proximity to an Internet-connected computing device including a web browser to run the patient portal 26 and/or electronic record source 28 to use the EMR software utility 14. In any event, the system 10 enables individuals with patient portal access to various beneficial functionalities of the EMR software utility 14.

Figure 2:
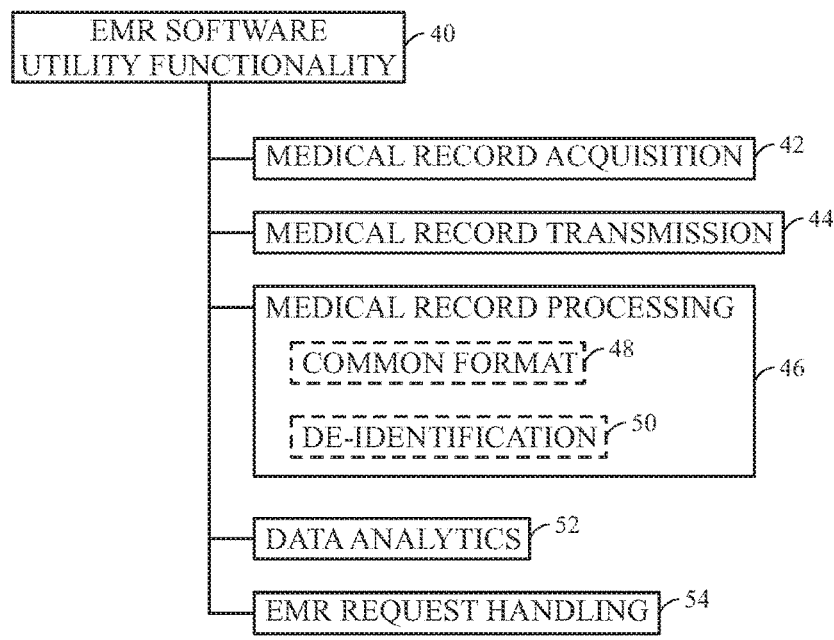
FIG. 2 is a schematic diagram of example functionalities of the EMR software utility of FIG. 1, in accordance with an aspect of the present disclosure.

For example, FIG. 2 is a schematic diagram of functionalities 40 of the EMR software utility 14 of FIG. 1. It should be understood that the functionalities 40 are examples and not intended to limit the capabilities of the EMR software utility 14. A first functionality 42 of the EMR software utility 14 functionalities 40 may include EMR 12 acquisition. As noted above, a user may login to the patient portal 26 or electronic record source 28 and select an EMR source provider system 16 that stores one or more desired EMRs 12. The user may enter their username and password as input to the EMR source provider system 16. The username and password may be validated by the EMR source provider system 16 and, if the credentials are valid, the EMR software utility 14 may execute one or more scripts to navigate the EMR source provider system 16 and obtain the desired content of the EMRs 12 and/or import the desired EMRs 12. No other authorization process may be used by the EMR source provider system 16 besides validating the credentials of the user. To be clear, other than validating credentials, present embodiments may explicitly exclude external authorization or, in some embodiments any other authorization, to execute the scripts to navigate the EMR source provider system 16 and obtain the desired content of the EMRs 12 and/or import the desired EMRs 12. In some embodiments, screen scraping techniques may be used to obtain the requested EMRs 12 or the EMR files may be imported from the source provider system to the EMR software utility 14. The EMRs 12 from numerous disparate provider systems 16 and/or other systems may be acquired by the EMR software utility 14 and stored in the database 18. In some embodiments, the EMRs 12 may not be stored and may be directly transmitted to the destination receiving provider system 16. In some embodiments, the EMR 12 content may be de-identified prior to being stored in the database 18. However, if the user desires to include the personal identifying information in the EMR 12 content, then the identification information may remain. In some embodiments, when personal identification information is included, the content of the EMR 12 may be encrypted or secured using public/private keys.

A second functionality 44 of the EMR software utility 14 functionalities 40 may include EMR transmission. EMR transmission may include sending the selected EMR 12 file to a selected destination (e.g., receiving provider system 16). The transmission functionality 44 may be available for receiving provider systems 16 that have passed the clearinghouse. The transmission functionality 44 may enable a user to move EMRs 12 between provider systems 16 directly and quickly without undue delay that results from time consuming authorization processes associated with traditional techniques and technology. For example, if a user makes an appointment at a new healthcare service provider, then the user may use the EMR software utility 14 to send existing EMRs 12 for the user from other provider systems 16 to the new healthcare service provider system 16 directly. In some instances, a fee may be charged for each transfer of an EMR 12. The fee may be paid by the user requesting the transfer or, in some instances, the receiving provider may pay the fee, depending on specific terms in certain agreements.

A third functionality 46 of the EMR software utility 14 functionalities 40 may include EMR 12 processing. EMR processing 46 may include reformatting imported EMRs 12 into a common format 48 that is accepted by provider systems 16 when the forms between the provider systems 16 are not consistent. The common format 48 may include certain key information that is extracted from the EMRs 12 using screen scraping techniques or by parsing file forms in certain formats (e.g., extensible markup language (XML)) for desired information elements. In other words, the EMR processing 46 may normalize disparate EMR forms to a common (e.g., standard) form. As previously noted, the imported EMRs 12 may be stored in a single data repository (e.g., database 18) in either the original format or the common format. Further, the EMR processing 46 may include de-identification 50 of the EMR 12 by removing personal identifiers prior to storing the de-identified EMR 12 content in the database 18. In this way, the database 18 may aggregate all de-identified health information for numerous patients, which may be leveraged by the EMR software utility 14 and/or other services (e.g., pharmaceutical, insurers, researchers) for data analytics.

Accordingly, in some embodiments, a fourth functionality 52 of the EMR software utility functionality 40 may include data analytics. Data analytics 52 may include identifying one or more correlations on the de-identified information and/or identified information for the user and similarly situated people (e.g., age, gender, race, medical history, allergies). That is, the EMR software utility 14 may analyze certain variables to make correlations. Certain correlations may include identifying patterns between health data, such as risk factors, behavior, incident timing, and the like to generate one or more recommendations. In some embodiments, the recommendations may include a suggestion to get screened for a particular illness. As discussed above, the data analytics 52 may account for other data 32 obtained from other devices 34. For example, the duration of time that a user spends driving a car every day (e.g., as communicated to the system 10 from a smart vehicle via data 32) may be a weighting factor in determining the recommendation. In one example, the data analytics 52 may analyze the de-identified information to determine that a new medication prescribed to the patient should not be taken when other conditions are present.

In certain embodiments, a fifth functionality 54 of the EMR software utility 14 functionality 40 may include EMR request handling. For example, certain programs and/or systems, such as the patient portal 26 and/or the electronic record source 28, may request to view and/or download one or more EMRs 12. EMR request handling 54 may determine whether credentials of the user have been validated and may retrieve the requested EMRs 12 to be viewed and/or downloaded from the database 18. As such, the process to view and/or download EMRs 12 may be more streamlined using the EMR software utility 14 than waiting on an authorization process or dealing with hardcopies of the medical records.

Figure 3:
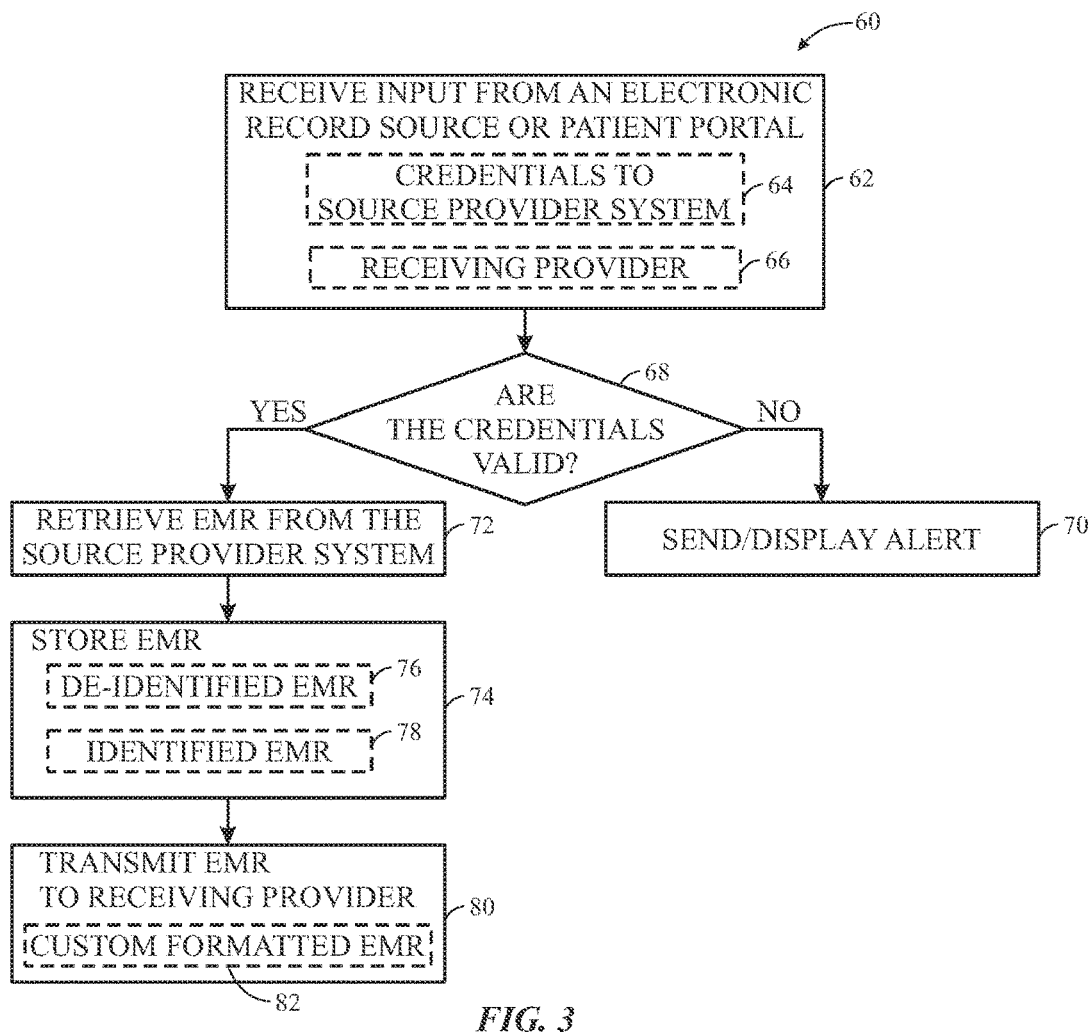
FIG. 3 is a process flow diagram illustrating an embodiment of a process of acquiring, storing, and/or transmitting EMRs between providers using the EMR software utility, in accordance with an aspect of the present disclosure.

FIG. 3 is a process flow diagram illustrating an embodiment of a process 60 of acquiring, storing, and/or transmitting EMRs 12 between provider systems 16 using the EMR software utility 14. It should be noted that the process 60 may be implemented as computer instructions (EMR software utility 14) stored on the memory 20 and executed by the processor 24. Although the following description of the process 60 is described with reference to the processor 24 of the server 22, it should be noted that the process 60 may be performed by other processors disposed on other devices that may be capable of communicating with the server 22, such as another computing device, the provider systems 16, or the like. Further, the processor 24 may be representative of a single processor or multiple processors working in coordination. Additionally, although the following process 60 describes a number of operations that may be performed, it should be noted that the process 60 may be performed in a variety of suitable orders and all of the operations may not be performed. It should be appreciated that the process 60 may be wholly executed by the server 22 or the execution may be distributed between the server 22 and another computing device.

Referring now to the process 60, the processor 24 may receive (block 62) inputs 30 from one or more request source (e.g., the electronic record source 28 and/or the patient portal 26). In some embodiments, the inputs 30 may include the credentials of the user to an EMR source provider system (block 64), a selection of a receiving provider system 16 (block 66), or some combination thereof. For example, in some embodiments, the user may wish to just import the EMRs 14 from a particular EMR source provider system. In such a scenario, the user may not select a destination receiving provider system 16. Instead, the user may input credentials on a landing page of the patient portal 26 and the EMR software utility 14 may import the EMRs 12 into the database 18 after the credentials have been validated by the EMR source provider system. On the other hand, when the user desires to send the EMRs 12 to other provider systems 16, the user may input a selection of the receiving provider system 16 as well as the credentials for the EMR source provider system where the desired EMRs are obtained. In some embodiments, the input may include a selection of specific content from the one or more EMRs 12 or a subset of the one or more EMRs 12 to import and/or transmit.

The processor 24 may determine (block 68) whether the credentials to the EMR source provider system 16 are valid.

For example, one or more scripts may be executed when the user clicks a submit button on a page of the patient portal 26. In one embodiment, the one or more scripts may enter the credentials as parameters into a query string appended to the end of the source provider website URL. If a response is received that the credentials are not valid, then the processor 24 may send/display (block 70) an alert indicating the same to the user via the patient portal 26 or the electronic record source 28. The alert may prompt the user that the username and/or password is incorrect and request the user to reenter the credentials. If a response is received that the credentials are valid, then the processor 24 may retrieve (block 72) (e.g., import) the desired EMR 12 from the provider website. In some embodiments, upon successful login to the source provider website, the one or more scripts may be specifically programmed to navigate the menus and/or submenus of the EMR source provider system (e.g., website) to view and/or import EMRs 12. In scenarios where the scripts view the EMRs 12, screen scraping techniques may be used to obtain the EMR content of interest. For example, the script may navigate to reports via the menus that show prescribed medications, lab results, medical history, allergies, and so forth, and scrape the content from the reports to generate the EMR 12 to import to the EMR software utility 14.

The processor 24 may store (block 74) the retrieved EMR 12 in the database 18. As previously discussed, the EMR 12 content may be de-identified (block 76) by the processor 24 removing personal identifiers from the content. De-identification may include identifying and deleting certain elements that include personal identifiers (e.g., name, social security) and their content in an XML document representing the EMR 12. De-identification may enable aggregating large amounts of health data for numerous individuals and allowing access to the anonymous data while conforming to certain governmental health regulations. Further, the processor 24 may store the EMR 12 data with the identification information (block 78) included at the request of the user. Aggregating the EMRs 12 from disparate sources may enable the personalized medical record to be created that provides a holistic view of the medical history of the user.

In addition, the processor 24 may transmit (block 80) the EMR 12 to the receiving provider system 16. In some embodiments, the EMR 12 may be reformatted into a common format (e.g., standard format) (block 82) prior to transmission. For example, the processor 24 may determine that the format of the imported EMR 12 and the accepted format of forms at the receiving provider system 16 are incompatible or different. Thus, the processor 24 may normalize the format of the EMR 12 by retaining elements of the document that are of interest while removing other undesired elements. In some embodiments, the processor 24 may transmit the retrieved EMRs 12 after reformatting the EMRs 12 to a common format that is accepted by the receiving provider system 16 when the formats are incompatible or different. Additionally, the processor 24 may transmit the retrieved EMRs 12 without reformatting the retrieved EMRs 12 when the formats are not different or incompatible. As a result, incompatibility issues between the various provider systems 16 may be removed. As should be appreciated, using the process 60 described above may enable a user to aggregate substantially all of their EMRs 12 in a centralized data repository (e.g., database 18) and to transfer EMRs 12 to any cleared provider system 16 at their discretion while avoiding a lengthy authorization process. The aggregation of the de-identified information may be useful to finding correlations and providing recommendations to patients, as well as to others (e.g., pharmaceutical manufacturers) to perform data mining, as described in the process below.

For example, FIG. 4 is a process flow diagram illustrating an embodiment of a process 90 of performing data analytics using aggregated EMRs 12 and/or other data 32. It should be noted that the process 90 may be implemented as computer instructions (e.g., the EMR software utility 14) stored on the memory 20 and executed by the processor 24. Although the following description of the process 90 is described with reference to the processor 24 of the server 22, it should be noted that the process 90 may be performed by other processors disposed on other devices that may be capable of communicating with the server 22, such as another computing device, the provider systems 16, or the like. Further, the processor 24 may be representative of a single processor or multiple processors acting together. Additionally, although the following process 90 describes a number of operations that may be performed, it should be noted that the process 90 may be performed in a variety of suitable orders and all of the operations may not be performed. It should be appreciated that the process 90 may be wholly executed by the server 22 or the execution may be distributed between the server 22 and another computing device.

Referring now to the process 90, the processor 24 may receive (block 92) EMRs 12 for respective patients and other data 32 for each respective patient. The processor 24 may aggregate (block 94) the EMRs 12 and other data 32 in the database 18 after de-identifying the content of the EMRs 12 and other data 32. The processor 24 may perform (block 96) data analytics for each respective patient and/or all patients using the aggregated data in the database 18. This may include determining correlations between patterns identified between data of similarly situated patients. Similarly situated patients may refer to patients with similar characteristics, such as age, gender, race, medical history, allergies, or the like. As the aggregated data grows, correlations and comparisons may be performed to provide the user with an idea of how the user is performing relative to other similarly situated people. The processor 24 may generate (block 98) one or more recommendations for the patient based at least on the data analytics. For example, one recommendation may include a suggestion to get screened for a particular illness based on recent symptoms, medical history, medications taken, blood pressure, heart rate, systematic or prolonged illnesses, or the like, compared to other people with similar information in the de-identified database 18. If a certain percentage of people with similar medical histories develop a certain illness (e.g., cancer) at a particular time, then the processor 24 may generate the recommendation to get screened for that illness and/or to modify exercise and diet. The combination of the EMRs 12 and the other data 32 may provide more granular ways to differentiate individuals that allows for more specific recommendations for screenings. Further, the processor 24 may send (block 100) the one or more recommendations to be displayed (e.g., by the patient portal 26). As may be appreciated, there are numerous scenarios in which the processor 24 may perform data analytics on aggregated de-identified information to generate one or more recommendations for a patient and the above discussion is meant to provide examples of such data analytics. It should be appreciated that the aggregation of data may provide a significant data source for research and advice.

Further, eligibility to participate in certain programs may be passed through families (e.g., parent to child). As parents pass eligibility over to their children, the processor 24 may begin making predictions and recommendations for the children based on genetic conditions and the medical history of the parents. That is, the EMRs 12 of the children may be used and compared with the aggregated data (e.g., EMRs 12 and data 32) of their parents to provide even more sophisticated data analytics and recommendations. For example, the processor 24 may recognize patterns in health issues that occur during the lifetime of the children as compared to their parents and can recommend particular screenings.

In additional embodiments, external entities, such as research entities, pharmaceutical manufacturers, or the like, may use the EMR software utility 14 to determine the overall health of the population or for a subset of the population. For example, the external entity may request access to the de-identified database 18 to perform data mining techniques and determine one or more correlations for specific sets of people (e.g., numerous users) or the population in certain areas of the world that are similarly situated. In some embodiments, the external entity may be charged a fee for each query to the database 18 or the fee may be flat for a period of time. It should be appreciated that the disclosed techniques may provide a powerful analytical tool for health research, among other things.

FIG. 5 is a process flow diagram illustrating an embodiment of a process 110 of automatically updating a personalized medical record for a patient using stored credentials. It should be noted that the process 110 may be implemented as computer instructions (EMR software utility 14) stored on the memory 20 and executed by the processor 24. Although the following description of the process 110 is described with reference to the processor 24 of the server 22, it should be noted that the process 110 may be performed by other processors disposed on other devices that may be capable of communicating with the server 22, such as another computing device, the provider systems 16, or the like. Additionally, although the following process 110 describes a number of operations that may be performed, it should be noted that the process 110 may be performed in a variety of suitable orders and all of the operations may not be performed. It should be appreciated that the process 110 may be wholly executed by the server 22 or the execution may be distributed between the server 22 and another computing device. Further, the processor 24 may represent a single processor or multiple processors acting in coordination.

Referring now to the process 110, the processor 24 may receive (block 112) a request to retain credentials to a source provider website. The request may specify a time line (block 114) that the processor 24 should retain the credentials and/or an indication of the EMR source provider website (block 116) associated with the retained credentials. The processor 24 may retrieve EMRs 12 from the source provider website at various time intervals through the specified time limit (block 114). The regularity of the retrieval may be any configurable amount of time. In some embodiments, the processor 24 may poll the source provider website to determine whether any EMR content has changed since the last update. When a change is identified, the EMR content may be retrieved (e.g., via screen scraping). In some embodiments, the processor 24 may login using the saved credentials and import the latest EMR 12 file for the patient and overwrite the previously stored EMR 12 in the database 12 with the newly imported file. In this way, the processor 24 may regularly update (block 120) a personalized medical record including numerous EMRs 12 from disparate sources.

Technical effects of some embodiments of the present disclosure generally enable retrieval and transmission of electronic record content from and to provider systems irrespective of the format or manufacture of the provider systems. Since the patient is performing the request directly, no consent/authorization process is utilized. In addition, transforming the EMRs into a common format which is specific and valuable to particular provider systems 16 may reduce the time and effort of extracting key information. Further, creating a de-identified database from imported EMR 12 content enables data analytics to confidentially provide recommendations to patients and may be of commercial interest to researchers, pharmaceutical manufacturers, and the like. Accordingly, present embodiments address Internet-centric and computer-centric issues with efficiency, availability, and confidentiality, among others.

While only certain features of the disclosure have been illustrated and described herein, many modifications and changes will occur to those skilled in the art. It is, therefore, to be understood that the appended claims are intended to cover all such modifications and changes as fall within the true spirit of the present disclosure.

The invention claimed is:

1. One or more non-transitory, computer-readable mediums storing computer instructions that, when executed by a processor, cause the processor to:
   receive one or more inputs from one or more request sources, wherein the one or more inputs comprise one or more user credentials to provide to an electronic medical record (EMR) source provider system;
   validate the one or more user credentials via communication with the EMR source provider system without an external authorization process;
   retrieve one or more EMRs from the EMR source provider system after the one or more user credentials are validated by the EMR source provider system;
   reformat the one or more EMRs into a common format to be compatible with both a receiving provider system and the EMR source provider system;
   store the reformatted one or more EMRs in a single data repository;
   receive a first set of data related to a first set of health characteristics of a user from a first device associated with the user;
   receive a second set of data related to a second set of health characteristics of the user from a second device associated with the user, wherein the second device is different from the first device, and wherein the first set of data is associated with a first weight and the second set of data is associated with a second weight, wherein the first weight is greater than the second weight;
   apply the first weight to the first set of data to generate a first weighted set of data;
   apply the second weight to the second set of data to generate a second weighted set of data;
   determine one or more correlations between the reformatted one or more EMRs, the first weighted set of data, the second weighted set of data, and a set of EMRs for similarly situated users, wherein the one or more correlations are indicative of a medical performance of the user relative to the similarly situated users;
   generate one or more recommendations for the user in response to the one or more correlations; and
   generate one or more visualizations representative of the one or more recommendations for display via an electronic display.

2. The one or more non-transitory, computer-readable mediums of claim 1, wherein the computer instructions that cause the processor to store the reformatted one or more EMRs in the single data repository comprises de-identifying the reformatted one or more EMRs by removing personal information associated with the user.

3. The one or more non-transitory, computer-readable mediums of claim 2, wherein the computer instructions are configured to cause the processor to:
data mine health data of the one or more de-identified reformatted EMRs to determine one or more additional correlations for one or more other users sharing one or more similar characteristics to the user; and
generate the one or more recommendations based on the one or more additional correlations.

4. The one or more non-transitory, computer-readable mediums of claim 1, wherein the EMR source provider system is configured to:
retain the one or more user credentials for a particular time;
update the one or more EMRs with the one or more reformatted EMRs by periodically polling for updated record content from the single data repository.

5. The one or more non-transitory, computer-readable mediums of claim 1, wherein the one or more request sources comprise a patient portal, an electronic record source, or some combination thereof.

6. The one or more non-transitory, computer-readable mediums of claim 1, wherein the computer instructions, when executed by the processor, cause the processor to:
transmit the one or more reformatted EMRs to the receiving provider system in response to an original format of the one or more EMRs being incompatible with the receiving provider system; and
transmit the one or more EMRs to the receiving provider system without reformatting the retrieved EMRs in response to the original format of the one or more EMRs not being incompatible with the receiving provider system.

7. The one or more non-transitory, computer-readable mediums of claim 1, wherein the computer instructions, when executed by the processor, cause the processor to:
receive the one or more user credentials from the one or more request sources;
retrieve the one or more EMRs from the EMR source provider system in response to the one or more user credentials being validated by the EMR source provider system without any separate authorization process;
reformat the one or more EMRs into the common format; and
store the reformatted one or more EMRs in the single data repository.

8. The one or more non-transitory, computer-readable mediums of claim 1, wherein the first set of health characteristics comprises data measured automatically via a wearable device.

9. The one or more non-transitory, computer-readable mediums of claim 1, wherein the second set of health characteristics comprises data measured manually via input from the user.

10. The one or more non-transitory, computer-readable mediums of claim 1,
wherein the computer instructions, when executed by the processor, cause the processor to:
receive a request to retain the one or more user credentials to provide to the EMR source provider system for a specified time limit;
retrieve one or more subsequent EMRs from the EMR source provider system at various time intervals throughout the specified time limit; and
update a personalized medical record with the one or more subsequent EMRs.

11. The one or more non-transitory, computer-readable mediums of claim 1,
wherein the computer instructions, when executed by the processor, cause the processor to modify the first weight, the second weight, or both, based on additional data associated with the first set of data, the second set of data, or both, received from the EMR source provider system.

12. A method, comprising:
receiving one or more inputs, via a processor, from one or more request sources, wherein the one or more inputs comprise one or more user credentials to provide to an electronic medical record (EMR) source provider system and a selection of a receiving provider system, and the one or more request sources comprise a patient portal or an electronic record source;
retrieving, via the processor, one or more EMRs from the EMR source provider system in response to the one or more user credentials being validated by the EMR source provider system without a separate authorization process;
reformatting, via the processor, the one or more EMRs into a common format to be compatible with both the receiving provider system and the EMR source provider system;
storing, via the processor, the reformatted one or more EMRs in a single data repository;
transmitting, via the processor, the reformatted one or more EMRs to the receiving provider system;
receiving, via the processor, a first set of data related to a first set of health characteristics from a first device associated with a user;
receiving, via the processor, a second set of data related to a second set of health characteristics of the user from a second device associated with the user, wherein the second device is different from the first device, and wherein the first set of data is associated with a first weight and the second set of data is associated with a second weight, wherein the first weight is greater than the second weight;
applying the first weight to the first set of data to generate a first weighted set of data and the second weight to the second set of data to generate a second weighted set of data;
determining, via the processor, one or more correlations between the reformatted one or more EMRs, the first weighted set of data, the second weighted set of data, and a set of EMRs for individuals having similar properties to the user wherein the one or more correlations are indicative of a medical performance of the user relative to the individuals having similar properties to the user;
generating, via the processor, one or more recommendations for the user in response to the one or more correlations; and
generating, via the processor, one or more visualizations representative of the one or more recommendation for display via an electronic display.

13. The method of claim 12, wherein the similar properties comprise a same occupation.

14. The method of claim 12, wherein reformatting the one or more EMRs into the common format comprises parsing file forms of the one or more EMRs to be in a standard format that is accepted by the receiving provider system.

15. The method of claim 12, comprising encrypting the one or more EMRs using a public and a private key pair in response to detecting that the one or more EMRs comprises personal identification information.

16. The method of claim 15, wherein determining the one or more correlations comprises identifying patterns between one or more risk factors of the individuals having the similar properties to the user, behavior of the individuals having the similar properties to the user, one or more incident timings of the individuals having the similar properties to the user, or a combination thereof.

17. The method of claim 12, comprising:
determining, via the processor, that a new medication prescribed to the user should not be taken based on the one or more correlations.

18. A system, comprising:
a processor configured to perform operations comprising:
receiving one or more inputs from one or more request sources, wherein the one or more inputs comprise one or more user credentials of a user to provide to an electronic medical record (EMR) source provider system and one or more receiving provider systems, wherein the one or more request sources comprise a patient portal or an electronic record source;
retrieving one or more EMRs from the EMR source provider system in response to the one or more user credentials being validated by the EMR source provider system;
reformatting the one or more EMRs into a common format that is compatible with both the EMR source provider system and the one or more receiving provider system storing the reformatted one or more EMRs in a single data repository;
transmitting the reformatted one or more EMRs to the one or more receiving provider systems;
receiving a first set of data related to a first set of health characteristics of the user from a first device associated with a user;
receiving a second set of data related to a second set of health characteristics of the user from a second device associated with the user, wherein the second device is different from the first device, and wherein the first set of data is associated with a first weight and the second set of data is associated with a second weight, wherein the first weight is greater than the second weight;
applying the first weight to the first set of data to generate a first weighted set of data and the second weight to the second set of data to generate a second weighted set of data;
determine one or more correlations between the reformatted one or more EMRs, the first weighted set of data, the second weighted set of data, and a set of EMRs for similarly situated users, wherein the one or more correlations are indicative of a medical performance of the user relative to the similarly situated users;
generating one or more recommendations for the user in response to the one or more correlations; and
generating one or more visualizations representative of the one or more recommendations for display via an electronic display.

19. The system of claim 18, wherein the one or more receiving provider systems are cleared by a clearinghouse prior to being placed on a list of cleared provider systems for the one or more request sources.

20. The system of claim 18, wherein the one or more EMRs are scraped for prescribed medications, lab results, medical history, or a combination thereof.

* * * * *